United States Patent [19]

Markos et al.

[11] 4,012,393
[45] Mar. 15, 1977

[54] 2-[5-(CYCLIC AMINO) ETHYL-10,11-DIHYDRO-5H-DIBENZO[a,d]-CYCLOHEPTEN-5-YL]-5-ALKYL-1,3,4-OXADIAZOLES AND CONGENERS

[75] Inventors: Charles S. Markos, Deerfield; Chung H. Yen, Skokie, both of Ill.

[73] Assignee: G. D. Searle & Co., Chicago, Ill.

[22] Filed: Mar. 22, 1976

[21] Appl. No.: 668,886

[52] U.S. Cl. ............... 260/293.54; 260/293.62; 260/307 G; 424/267; 424/269

[51] Int. Cl.² ...................................... C07D 413/06

[58] Field of Search ............. 260/293.54, 293.62, 260/307 G

[56] References Cited

UNITED STATES PATENTS 3,917,615  11/1975  Adelstein ............... 260/293.54

*Primary Examiner*—G. Thomas Todd
*Attorney, Agent, or Firm*—John J. Kolano

[57] ABSTRACT

This invention encompasses novel 2-[5-(cyclic amino) ethyl-10,11-dihydro-5H-dibenzo[a,d]cyclophenten-5-yl]-5-alkyl-1,3,4-oxadiazoles and congeners, useful as anti-diarrheal agents.

5 Claims, No Drawings

2-[5-(CYCLIC AMINO) ETHYL-10,11-DIHYDRO-5H-DIBENZO[a,d]-CYCLOHEPTEN-5-YL]-5-ALKYL-1,3,4-OXADIAZOLES AND CONGENERS

The present invention is concerned with 2-[5-(cyclic amino)ethyl-10,11-dihydro-5H-dibenzo[a,d]cyclohepten-5-yl]-5-alkyl-1,3,4-oxadiazoles and congeners. More particularly, this invention is concerned with compounds of the formula

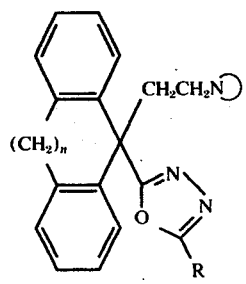

(I)

wherein R is lower alkyl containing 1 to 6 carbon atoms; n is the integer 2 or 3; and -N⟩ is a cyclic secondary amine residue selected from the group consisting of azabicycloalkyl containing 6 to 9 carbon atoms and having at least 5 atoms in each ring, pyrrolidino, piperidino and hexamethylenimino.

Particularly preferred compounds of this invention are those of the formula

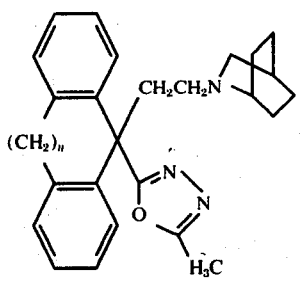

(II)

wherein n is the integer 2 or 3.

The lower alkyl groups referred to hereinabove contain 1 to 6 carbon atoms and are exemplified by methyl, ethyl, propyl, butyl, pentyl, hexyl and the corresponding branched chain isomers thereof.

The cyclic secondary amine residues which are azabicycloalkyl groups containing 6 to 9 carbon atoms and having at least 5 atoms in each ring are exemplified by groups such as 7-azabicyclo[2.2.1]hept-7-yl, 2-azabicyclo[2.2.2]oct-2-yl, 2-azabicyclo[3.2.1]oct-2-yl, 3-azabicyclo[3.2.1]oct-3-yl, 6-azabicyclo[3.2.1]oct-6yl, 3-azabicyclo[3.2.2]non-3-yl, 8-azabicyclo]4.3.0]-non-8-yl, 2-azabicyclo[3.2.2]non-2-yl, 2azabicyclo[3.3.1]non-2-yl, 3-azabicyclo[3.3.1]non-3-yl, 2-azabicyclo[4.3.0]non-3-yl, 7-azabicyclo[4.3.0]non-7-yl, 8-azabicyclo[4.3.1]dec-8-yl, 2-azabicyclo[4.4.0]-dec-2-yl, and 7-azabicyclo[4.2.2]dec-7-yl.

Equivalent to the compounds of formulas (I) and (II) for the purposes of this invention are the pharmaceutically acceptable acid addition salts thereof. Such acid addition salts can be derived from a variety of inorganic and organic acids such as sulfuric, phosphoric, hydrochloric, hydrobromic, hydroiodic, sulfamic, citric, lactic, pyruvic, oxalic, maleic, succinic, tartaric, cinnamic, acetic, benzoic, salicylic, gluconic, ascorbic and related acids.

The compounds of the present invention are useful in consequence of their valuable pharmacological properties. They are, for example, anti-diarrheal agents as evidenced by their ability to inhibit gastrointestinal motility as set out in the following tests.

Charcoal Meal Test

The method used for this assay is a modification of the techniques previously described by Macht and Barba-Gose, J. Amer. Pharm. Ass., 20, 558 (1931), and Janssen and Jageneau, J. Pharm. Pharmacol., 9, 381 (1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

Castor Oil-Induced Diarrhea in the Rat

Adult Charles River male rats are fasted in community cages for 24 hours prior to the test, with free access to water. The test compound is then administered intragastrically (suspended in 0.5% methyl cellulose) one hour prior to the intragastric administration of a dose of 1.0 ml. castor oil per rat. The rats are then observed for the presence or absence of diarrhea at hourly intervals for up to 8 hours past the castor oil administration. Using the method of Berkson (1953), the median effective dose ($ED_{50}$) values are calculated at each hourly interval for the test compound.

In addition to their anti-diarrheal activity, the compounds of this invention demonstrate little or no analgesic activity at the test doses. The assessment of this activity is conducted by the following assay:

Tail Clip Test

A special clip is applied to the base of the tail of an adult male mouse weighting 18–25 grams and the time for the animal to turn around to bite at the clip is measured. The sensitivity of each mouse is determined one half hour prior to drug administration and only those mice attempting to bite the clip are included in the experiment. The test compound is then administered either intragastrically or intraperitoneally and the response to placement of the clip is determined at 30, 60, 90 and 120 minutes after treatment. A response is considered positive if the animal takes more than 2 times the predrug time to bite at the clip at any of these time intervals. A test compound is considered active when 50 percent or more of the animals used show a positive response.

A representative compound of this invention which is particularly active in the above Charcoal Meal Test anti-diarrheal assay is 2-[5-(2-azabicyclo[2.2.2]oct-2- yl)-10,11-dihydro-5H-dibenzo[a,d]cyclohepten-5-yl]-5-methyl-1,3,4-oxadiazole. This compound also exhibits only slight analgesic effects at a dose of 100 ml./kg. administered orally.

The compounds of formula (I) may be combined with various pharmaceutical carriers to provide compositions suitable for use in the treatment of diarrhea. The dosage of these compounds is dependent upon various factors, such as the particular compound employed and the patients's individual response. Typical dosages for use as an anti-diarrheal agent vary from 0.1 to 25 mg./kg. per day administered orally.

The compounds of the present invention are conveniently prepared by the reaction sequence set out in Scheme A.

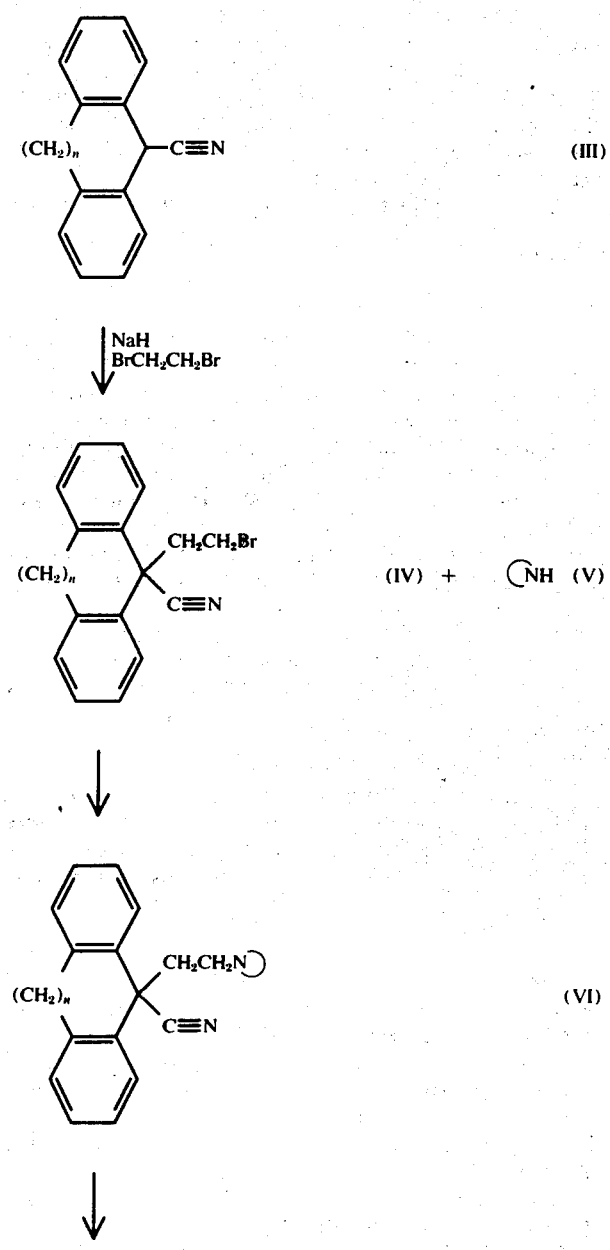

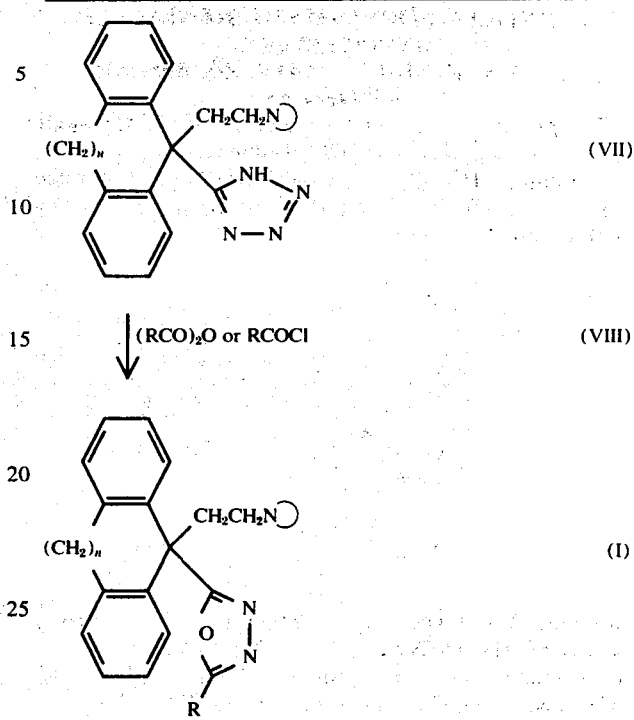

As shown in Scheme A, the nitrile of formula (III) is contacted with sodium hydride and 1,2-dibromoethane to provide the intermediate of formula (IV).

The intermediate of formula (IV) is then reacted with the appropriate secondary amine of formula (V) wherein N is defined as hereinabove to form the (cyclic amino(ethyl nitrile of formula (VI). Depending on the nature of the reactants, it is possible to carry out this reaction in the presence or absence of a solvent. The use of a solvent is, however, generally preferred. Suitable solvents, include, but are not limited to, benzene, methanol, methyl ethyl ketone and mixtures of dimethylsulfoxide and water. Time and temperature are not critical factors for the conduct of the reaction, typical temperatures varying from room temperature to reflux, and typical times being in the range of 0.5–24 hours.

These novel (cyclic amino)ethyl nitrile intermediates of formula (VI) are additionally useful as anti-diarrheal agents which possess little or no analgesic effects at the test doses. A representative compound, 5-cyano-5-[2-(2-azabicyclo[2.2.2]oct2-yl)ethyl]-10,11-dihydro-5H-dibenzo[a,d]cycloheptene hydrochloride is active in the Charcoal Meal Test and shows only slight analgesic effects at a dose of 100 mg./kg. administered orally.

The (cyclic amino(ethyl nitrile of formula (VI) is then reacted with an azide ion by methods similar to those described by Moersch and Morrow, J. Med. Chem., 10, 149 (1967) to obtain the tetrazole of formula (VII).

The tetrazoles of formula (VII) are converted to the compounds of formula (I) by reaction with an appropriate acylating agent of formula (VIII) wherein R is defined as hereinbefore. This reaction is conveniently conducted in an organic solvent, a particularly preferred solvent being pyridine.

Throughout the formulas illustrated in Scheme A, the variant n is as defined hereinbefore.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees Centigrade (°C.) and relative amounts in parts by weight except as otherwise noted.

EXAMPLE 1

To 5.0 parts of a 57% suspension of sodium hydride in mineral oil which has been washed three times with portions of n-pentane under a nitrogen atmosphere is added 360 parts dry tetrahydrofuran followed by 21.9 parts 5-cyano-10,11-dihydro-5H-dibenzo[a,d]cycloheptene. Then, a solution of 20.0 parts 1,2-dibromoethane in 18 parts tetrahydrofuran is added and the reaction mixture heated at reflux. An additional 4 parts of a 57% suspension of sodium hydride in mineral oil and 10 parts 1,2-dibromoethane are added and refluxing continued for an additional 18 hours. After cooling, 100 parts by volume of a saturated sodium acetate solution is added and the organic layer separated. The solvents are removed from the organic layer in vacuo and the residue dissolved in ether. The ethereal solution is washed three times with dilute sodium chloride solution, dried over anhydrous sodium sulfate, filtered and the solvents removed in vacuo. The resultant oil is purified by column chromatography using a 50:50 mixture of methylene chloride and n-hexane as eluant to give 5-cyano-5-(2-bromoethyl)-10,11-dihydro-5H-dibenzo[a,d]cycloheptene. This compound is represented by the following structural formula.

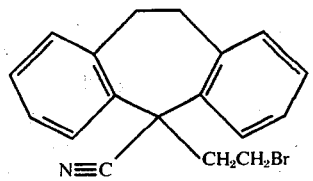

EXAMPLE 2

A mixture of 6.5 parts 5-cyano-5-(2-bromoethyl)10,11-dihydro-5H-dibenzo[a,d]cycloheptene, 4.0 parts 2-azabicyclo[2.2.2]octane hydrochloride and 4.0 parts potassium carbonate in 88 parts N,N-dimethylsulfoxide and 20 parts water is heated at reflux for about 4 hours. After cooling, the reaction mixture is diluted with water, resulting in the formation of an oil. The water layer is decanted and the oil dissolved in ethyl ether. The ethereal solution is washed twice with water, once with a saturated sodium chloride solution, dried over anhydrous sodium sulfate and filtered. The solvent is removed to give an oil which is treated with a solution of hydrogen chloride in isopropanol. Addition of ethyl ether results in a precipitate that is separated, washed with ether and dried to afford-5-cyano-5[2-(2-azabicyclo[2.2.2]oct-2-yl)ethyl]-10,11-dihydro-5H-dibenzo[a,d]cycloheptene hydrochloride. This compound is represented by the following structural formula.

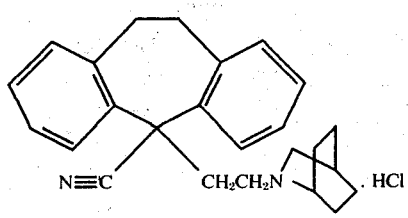

EXAMPLE 3

A mixture of 2.0 parts 5-cyano-5-[(2-azabicyclo[2.2.2]oct-2-yl)ethyl]-10,11-dihydro-5H-dibenzo[a,d]cycloheptene hydrochloride, 0.5 parts sodium azide, 0.40 part ammonium chloride, 0.02 part lithium chloride is dissolved in 7 parts N,N-dimethylformamide. Then, 0.5 part triethyl amine is added and the mixture is heated at reflux temperature with stirring for 18 hours under a nitrogen atmosphere. After cooling, the resultant precipitate is collected, washed successively with with cold N,N-dimethylformamide, water, and air-dried to afford 5-{-5-[2-(2-azabicyclo[2.2.2]oct-2-yl)ethyl]-10,11-dihydro-5H-dibenzo[a,d]cyclohepten-5-yl}-1H-tetrazole. This compound is represented by the following structural formula.

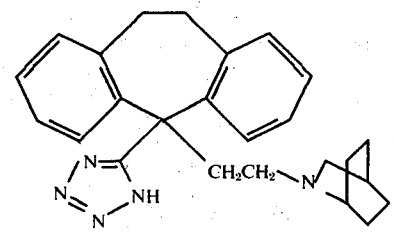

EXAMPLE 4

A mixture of 0.75 part 5-[5-(2-azabicyclo[2.2.2]oct2-yl)-10,11-dihydro-5H-dibenzo[a,d]cyclohepten-5-yl]-1H-tetrazole, 8 parts pyridine and 4 parts acetic anhydride is heated at reflux for 3 hours. After cooling, 3 parts water is added and the solvents removed in vacuo to leave a semi-solid residue. This residue is dissolved in ether and extracted with water. The water extract is separated, reduced to dryness, combined with 115 parts benzene, and heated at reflux under a Dean-Stark water separator. The benzene solution is then filtered and the solvents removed in vacuo to leave an oil. This oil is chromatographed on alumina using 10:90 ethyl acetatebenzene as eluant to give a colorless oil that is dissolved in a mixture of acetone and petroleum ether and allowed to stand. The resulting crystals are filtered, washed with cold petroleum ether and air-dried to afford 2-{5-[2-(2-azabicylo[2.2.2]oct-2-yl)ethyl]-10.11-dihydro-5H-dibenzo[a,d]cyclohepten-5-yl}-5-methyl-1,3,4-oxadiazole. This compound melts at 157–158° C. and is represented by the following structural formula.

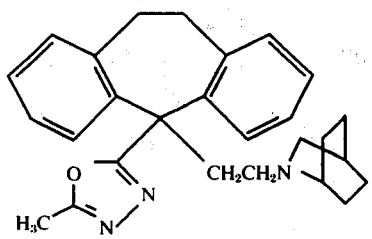

EXAMPLE 5

2.5 Parts of 57% suspension of sodium hydride in mineral oil is washed three times with n-pentane under a nitrogen atmosphere. To this dry sodium hydride is then added 88 parts anhydrous tetrahydrofuran, followed by 4.4 parts 5-cyano5,6,7,12-tetrahydrodibenzo[a,d[cyclooctene and 4.5 parts 1,2-dibromoethane. After warming for a short period, an additional 4 parts 1,2-dibromoethane is added and the warming continued for a further 18 hours. After cooling, 25 parts by volume of a saturated sodium acetate solution is added. The organic layer is then separated, stripped of solvents in vacuo and dissolved in 80 parts benzene. This benzene solution is washed three times with dilute sodium acetate solution, once with saturated sodium chloride solution, dried over anhydrous sodium sulfate, filtered and stripped of solvent in vacuo. The residue is dissolved in hot isopropanol, filtered and reduced in volume in vacuo to about 25 ml. Cooling results in a precipitate which is separated and washed with cold isopropanol to afford 12cyano-12(2-bromoethyl)-5,6,7,12-tetrahydrodibenzo[a,d]cyclooctene.

EXAMPLE 6

3.1 Parts 12-cyano-12-(2-bromoethyl)-5,6,7,12-tetrahydrodibenzo[a,d]cyclooctene, 1.8 parts 2-azabicyclo[2.2.2]octane hydrochloride, 1.8 parts potassium carbonate, 44 parts dimethylsulfoxide and 10 parts water are combined, heated at 100° C. for about 4 hours, and then poured into an ice-water mixture. The resulting gummy precipitate is dissolved in a mixture of ethyl ether and methylene chloride. The organic phase is separated, washed three times with water, dried with sodium sulfate, filtered, and the solvents removed to leave an oil. This oil is dissolved with a solution of HCl in isopropanol, and precipitated with ethyl ether to give 12-cyano12-[2-(2-azabicyclo[2.2.2]oct-2-yl)ethyl]-5,6,7,12-tetrahydrodibenzo[a,d]cyclooctene hydrochloride. This compound is represented by the following structural formula.

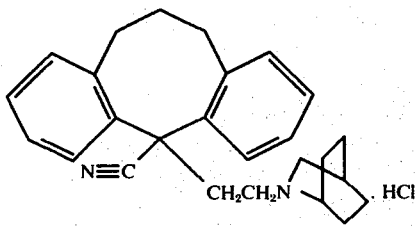

EXAMPLE 7

To a mixture of 1.3 parts 12-cyano-12-[2-(2-azabicyclo[2.2.2]oct-2-yl)ethyl]-5,6,7,12-tetrahydrodibenzo[a,d]cyclooctene hydrochloride, 0.35 part sodium azide, 0.28 part ammonium chloride and 0.015 part lithium chloride is added 5.5 parts N,N-dimethylformamide followed by 0.33 part triethylamine. Then, the mixture is heated at reflux for 4 hours. After cooling, the precipitate is collected, washed with cold N,N-dimethylformamide, and mixed with water to give a filterable solid. The solid is separated, washed with water, triturated with dilute hydrochloric acid, refiltered and washed with water to yield 5-{12-[2-(2-azabicyclo[2.2.2]oct-2-yl)ethyl]-5,6,7,12-tetrahydrodibenzo[a,d]cycloocten-12-yl}-1H-tetrazole. This compound is represented by the following structural formula.

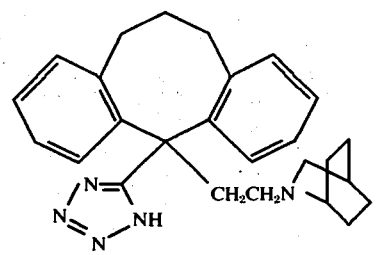

EXAMPLE 8

A mixture of 1.1 parts 5-{12-[2-(2-azabicyclo[2.2.2]oct-2-yl)ethyl]-5,6,7,12-tetrahydrodibenzo[a,d]cycloocten-12-yl}-1H-tetrazole, 10 parts pyridine and 5 parts acetic anhydride is heated to 100° C. for 2 hours. The reaction is then quenched with water, and the solvents removed in vacuo. The residue is chromatographed on alumina using a 10:90 ethyl acetate-benzene mixture as eluant. The oil obtained is dissolved in a mixture of acetone and petroleum ether and allowed to stand, resulting in a crystalline precipitate. The precipitate is filtered and dried to afford 2-{2-[2-(2-azabicyclo[2.2.2]oct-2-yl)ethyl]-5,6,7,12-tetrahydrodibenzo[a,d]cycloocten-12-yl}-5-methyl.1,3,4-oxadiazole, melting at about 176-179° C. and represented by the following structural formula.

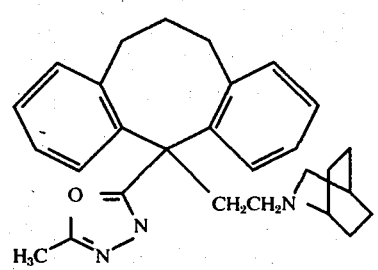

EXAMPLE 9

Repetition of the procedure of Example 2 using an equivalent quantity of piperidine hydrochloride in place of the 2-azabicyclo[2.2.2]octane hydrochloride affords 5-cyano-5-(2-piperidinoethyl)-10,11-dihydro-5H-dibenzo[a,d]cycloheptane hydrochloride.

EXAMPLE 10

Substitution of an equivalent quantity of 5-cyano-5-[2-piperidinoethyl]-10,11-dihydro-5H-dibenzo[a,d]cycloheptene hydrochloride for the 5-cyano-5-[2-(2-azabicyclo[2.2.2]oct-2-yl)ethyl]-10.11-dihydro-5H-dibenzo[a,d]cycloheptene hydrochloride of Example 3 and substantial repetition of the procedure detailed therein affords 5[5-(2-piperidinoethyl)-10.11-dihydro-5H-dibenzo[a,d]cyclohepten-5-yl]-1H-tetrazole.

EXAMPLE 11

When an equivalent quantity of 5[5-(2-piperidinoethyl)-10.11-dihydro-5H-dibenzo[a,d]cyclohepten-5-yl]-1H-tetrazole is treated according to the procedure of Example 4 using propionic anhydride in place of the acetic anhydride, there is obtained 2-[5-(2-piperidinoethyl)-10,11-dihydro-5H-dibenzo[a,d]cyclohepten-5-yl]-5-ethyl-1,3,4-oxadiazole This compound is represented by the following structural formula.

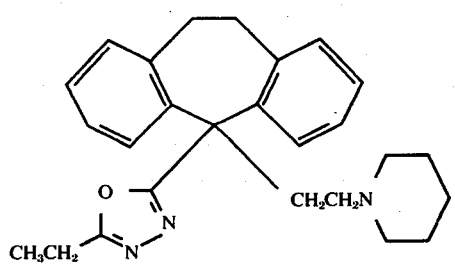

EXAMPLE 12

Repetition of the procedure of Example 2 using an equivalent quantity of pyrrolidine hydrochloride in place of the 2-azabicyclo[2.2.2]octane hydrochloride affords 5-cyano-5-(2-pyrrolidinoethyl)-10,11-dihydro-5H-dibenzo[a,d]cycloheptene hydrochloride.

EXAMPLE 13

Substitution of an equivalent quantity of 5-cyano-5-(2-pyrrolidinoethyl)-10,11-dihydro-5H-dibenzo[a,d]cycloheptene hydrochloride for the 5-cyano-5-[2-(2-azabicyclo[2.2.2]oct-2-yl)ethyl]-10,11-dihydro-5H-dibenzo[a,d]cycloheptene hydrochloride of Example 3 and substantial repetition of the procedure detailed therein affords 5-[5-(2-pyrrolidinoethyl)-10.11-dihydro-5H-dibenzo[a,d]cyclohepten-5-yl]-1H-tetrazole.

EXAMPLE 14 when an equivalent quantity of 5-[5-(2-pyrrolidinoethyl)-10,11-dihydro-5H-dibenzo[a,d]cyclohepten-5-yl]-1H tetrazole is treated according to the procedure of Example 4, there is obtained 2-[5-(2-pyrrolidinoethyl)-10,11-dihydro5H-dibenzo[a,d]cyclohepten-5-yl]-5-methyl-1,3,4-oxadiazole. This compound is represented by the following structural formula.

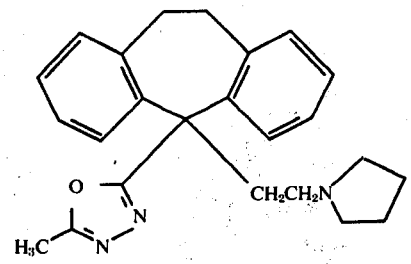

EXAMPLE 15

Repetition of the procedure of Example 6 using an equivalent quantity of 7-azabicyclo[2.2.1]heptane hydrochloride in place of the 2-azabicyclo[2.2.2]octane hydrochloride affords 12-cyano-12-[2-(7-azabicyclo[2.2.1]hept-7-yl)ethyl]-5,6,7,12-tetrahydrodibenzo[a,d]cyclooctene hydrochloride.

EXAMPLE 16

Substitution of an equivalent quantity of 12-cyano-12-[2-(7-azabicyclo[2.2.1]hept-7-yl)ethyl]-5,6,7,12-tetrahydrodibenzo[a,d]cyclooctene hydrochloride for the 12-cyano-12[2-(2-azabicyclo[2.2.2]oct-2-yl)ethyl]-5,6,7,12-tetrahydrodibenzo[a,d]cyclooctene hydrochloride of Example 7 and substantial repetition of the procedure detailed therein affords 5-{12-[2(7-azabicyclo[2.2.1]hept-7-yl)ethyl]-5,6,7,12tetrahydrodibenzo[a,d]cycloocten-12-yl}-1H-tetrazole.

EXAMPLE 17 when an equivalent quantity of 5-{12-[2(7-azabicyclo[2.2.1]hept-7-yl)ethyl]-5,6,7,12-tetrahydrodibenzo[a,d]cycloocten-12-yl}-1H-tetrazole is treated according to the procedure of Example 8, there is obtained 5-{12-[2-7-azabicyclo[2.2.1]hept-7-yl)ethyl]-5,6,7,12-tetrahydrodibenzo[a,d]cycloocten-12-yl}-2-methyl-1,3,4-oxadiazole. This compound is represented by the following structural formula.

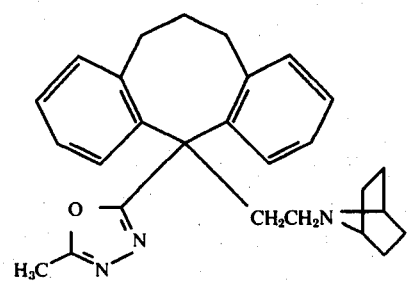

What is claimed is:
1. A compound of the formula

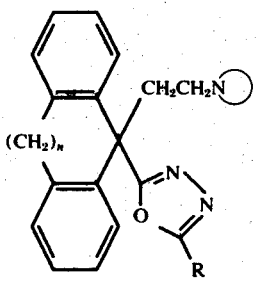

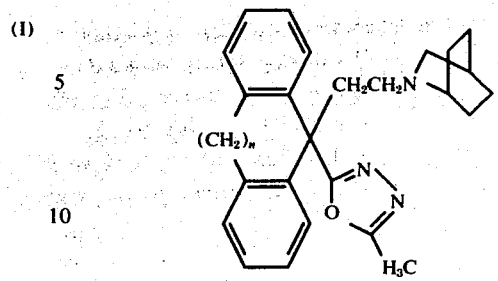

wherein R is lower alkyl containing 1 to 6 carbon atoms; n is the integer 2 or 3; and -N◯ is a cyclic secondary amine residue selected from the group consisting of azabicycloalkyl containing 6 to 9 carbon atoms and having at least 5 atoms in each ring, pyrrolidino, piperidino and hexamethyleneimino.

2. A compound according to claim 1 of the formula wherein n is the integer 2 or 3.

3. The compound according to claim 1 which is 2-{5-[2-(2-azabicyclo[2.2.2]oct-2-yl)ethyl]-10,11-dihydro-5H-dibenzo[a,d]cyclohepten-5-yl}-5-methyl-1,3,4-oxadiazole.

4. The compound according to claim 1 which is 2-{12-[2-(2-azabicyclo[2.2.2]oct-2-yl)ethyl]-5,6,7,12-tetrahydrodibenzo[a,d]cycloocten-12-yl}-5-methyl-1,3,4-oxadiazole.

5. The compound which is 5-cyano-5-[2(2-azabicyclo[2.2.2]oct-2-yl)ethyl]-10,11-dihydro-5H-dibenzo[a,d]cycloheptene hydrochloride.

* * * * *